United States Patent [19]

Christiansen

[11] 4,055,562

[45] Oct. 25, 1977

[54] PROCESS FOR PREPARING PREGN-20-YNE COMPOUNDS AND NOVEL PRODUCT PRODUCED THEREBY

[75] Inventor: Robert George Christiansen, Schodack, N.Y.

[73] Assignee: Sterling Drug Inc., New York, N.Y.

[21] Appl. No.: 691,196

[22] Filed: May 28, 1976

Related U.S. Application Data

[63] Continuation-in-part of Ser. No. 619,579, Oct. 6, 1975, abandoned.

[51] Int. Cl.$^2$ .............................................. C07J 71/00
[52] U.S. Cl. ........................................... 260/239.55 R
[58] Field of Search ...................... 260/239.55 R, 397.4

[56] References Cited

U.S. PATENT DOCUMENTS 3,790,564  2/1974  Pierdet et al. ............... 260/239.55 C

FOREIGN PATENT DOCUMENTS 842,676  7/1960  United Kingdom .............. 260/397.4

OTHER PUBLICATIONS

JACS, vol. 83 (1961) p. 4663–4664, by Fried et al.

Primary Examiner—Elbert L. Roberts
Attorney, Agent, or Firm—Thomas L. Johnson; B. Woodrow Wyatt

[57] ABSTRACT

A process for preparing 17$\beta$-hydroxysteroido[2,3-d]isoxazoles substituted at the 17$\alpha$-position by an ethynyl or substituted ethynyl group comprising reacting a 17-oxosteroido[2,3-d]isoxazole with the appropriate ethynylmagnesium halide, substituted ethynylmagnesium halide, monolithium acetylide or substituted monolithium acetylide. The process affords a novel compound, 21-trifluoromethyl-17$\alpha$-pregn-4-en-20-yno[2,3-d]isoxazol-17-ol, which has estrogenic activity.

11 Claims, No Drawings

PROCESS FOR PREPARING PREGN-20-YNE COMPOUNDS AND NOVEL PRODUCT PRODUCED THEREBY

This application is a continuation-in-part of application Ser. No. 619,579, filed Oct. 6, 1975, now abandoned.

BACKGROUND OF THE INVENTION a. Field of the Invention

This invention relates to a new process for preparing certain pregn-20-yne compounds and to a novel steroid produced thereby.

b. Description of the Prior Art

Clinton and Manson U.S. Pat. No. 3,135,743 discloses a series of steroido[2,3-d]isoxazoles, useful as endocrinological agents, including compounds of the formulas:

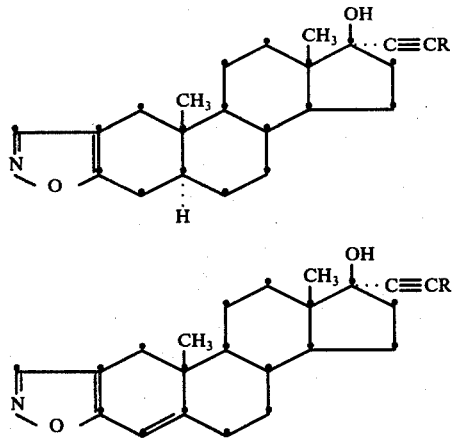

where R is H or $CH_3$. The compounds of formulas I and II were prepared by formation of the isoxazole ring from the corresponding 3-oxo steroids, 17α-(C≡CR)-17β-hydroxyandrostan-3-one or 17α-(C≡CR)-17β-hydroxyandrost-4-en-3-one. The 3-oxo steroid was caused to react with ethyl formate in the presence of a base to form the 2-hydroxymethylene derivative. The latter was then interacted with hydroxylamine to form the steroido[2,3-d]isoxazole nucleus.

Clinton and Manson U.S. Pat. Nos. 3,135,743 and 3,296,255 teach that steroido[2,3-d]isoxazoles are cleaved sith strong bases to form 2-cyano-3-oxo steroids.

The formation of 17α-ethynyl-17β-hydroxy steroids by reaction of 17-oxo steroids with ethynyl Grignard reagents or alkali metal acetylides is known, e.g., Pierdet U.S. Pat. No. 3,790,564, but the reaction has never been applied to 17-oxo steroids containing an isoxazole moiety.

SUMMARY OF THE INVENTION

In its process aspect, the invention relates to a process for preparing a 17α-(2-R-ethynyl)-17β-hydroxysteroido[2,3-d]isoxazole which comprises reacting a 17-oxosteroido[2,3-d]isoxazole devoid of substituents, other than the 17-oxo group, reactive with organometallic compounds, with (2-R-ethynyl)magnesium halide or (2-R-ethynyl)lithium wherein R is hydrogen, methyl or trifluoromethyl.

In a preferred process aspect, the invention relates to a process for preparing a compound of formula I or II, where R is H, $CH_3$ or $CF_3$, which comprises treating a compound of the formula

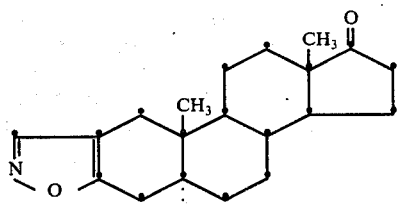

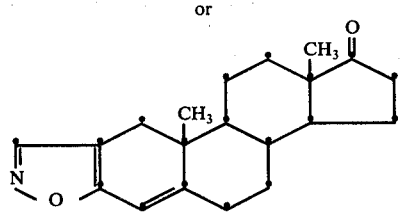

with a compound of the formula X-Mg-C≡CR where X is chlorine, bromine or iodine, or a compound of the formula LiC≡CR, in an inert solvent under anhydrous conditions.

In a further process aspect, the invention relates to a process for preparing 4,4-dimethyl-17α-pregn-5-en-20-yno[2,3-d]isoxazol-17β-ol which comprises treating 4,4-dimethylandrost-5-eno[2,3-d]isoxazol-17-one with ethynylmagnesium halide in an inert solvent under anhydrous conditions.

In its composition of matter aspect, the invention relates to the novel compound, 21-trifluoromethyl-17α-pregn-4-en-20-yno[2,3-d]isoxazole (formula II where R is $CF_3$), useful as an estrogenic agent.

DETAILED DESCRIPTION INCLUSIVE OF PREFERRED EMBODIMENTS

In view of the known chemical properties of isoxazoles, including steroido[2,3-d]isoxazoles, in particular their tendency to be cleaved in the presence of a base, it was surprising to find that 17-oxosteroido[2,3-d]isoxazoles can be caused to react with an ethynylmagnesium halide or lithium acetylide to produce the corresponding 17α-ethynyl-17β-hydroxysteroido[2,3-d]isoxazole without opening the isoxazole ring.

Any 17-oxosteroido[2,3-d]isoxazole, otherwise devoid of substituents reactive with organometallic compounds such as carboxyl groups or additional oxo groups, can participate in the reaction. In the ethynylmagnesium halide or monolithium acetylide, one of the acetylenic hydrogens is replaced by the magnesium halide moiety or lithium atom and the other of the acetylenic hydrogens is either left intact or replaced by an inert substituent such as alkyl or trifluoromethyl.

The reaction between the 17-oxosteroido[2,3-d]isoxazole and ethynylmagnesium halide is carried out in an inert solvent such as ether or tetrahydrofuran under anhydrous conditions. The reaction takes place readily under ambient temperature conditions or slightly above, preferably in an inert atmosphere such as nitrogen. A molar excess of Grignard reagent is used for optimum yields.

The reaction between the 17-oxosteroido[2,3-d]isoxazole and monolithium acetylide is carried out in an inert solvent under anhydrous conditions. The reaction takes place readily at ambient temperatures and is preferably carried out at substantially reduced temperature (−70° to −40° C.) to minimize side reactions such as cleavage of the isoxazole ring. A molar excess of monolithium acetylide is used for optimum yields.

The ethynylmagnesium halide or monolithium acetylide is conveniently prepared in situ from a commercially available alkylmagnesium halide or alkyllithium, e.g. ethylmagnesium bromide or butyllithium, and acetylene or a monosubstituted acetylene whereby replacement of the alkyl moiety by the ethynyl moiety in the Grignard reagent or alkyllithium is effected.

The reaction can, if desired, be carried out in the presence of magnesium chloride which has the property of suppressing any competing O-alkylation reaction.

The following examples will further illustrate the invention.

EXAMPLE 1

Preparation of 17α-pregn-4-en-20-yno[2,3-d]isoxazol-17β-ol [II; R is H].

Ethylmagnesium bromide (0.015 mole, 5 ml. of 3 molar in ether) was added to 100 ml. of dry tetrahydrofuran kept under a nitrogen atmosphere. The reaction vessel was closed by a soda-lime drying tube, and the solution was stirred while cooled in ice externally. Acetylene from a cylinder was passed through a column containing 100 g. of basic alumina and then into the stirred solution. The weight of the cylinder was followed to determine when an excess of acetylene (0.04 mole or more) had been passed into the solution. The cooling bath was removed and 1.5 g. (0.005 mole) of 17-oxoandrost-4-eno[2,3-d]isoxazole [Manson et al., J. Med. Chem. 6, 1-9 (1963)] in 50 ml. of dry benzene was added from a dropping funnel to the Grignard solution. The reaction mixture was stirred at room temperature for one hour and allowed to stand for about 16 hours. Saturated aqueous ammonium chloride solution was then stirred into the reaction mixture, the aqueous layer separated and 500 ml. of benzene added to the organic layer. The latter was extracted with water and aqueous sodium bicarbonate solution, dried over anhydrous magnesium sulfate, filtered and concentrated. The residue was crystallized from ethyl acetate-ether to give 0.70 g. of 17α-pregn-4-en-20-yno[2,3-d]isoxazol-17β-ol, m.p. 205°-212° C. (hot stage) with infrared and nuclear magnetic resonance spectra identical with those of the same compound described by Manson et al, loc. cit., there named as 17α-ethinyl-17β-hydroxyandrost-4-eno[2,3-d]isoxazole.

EXAMPLE 2 a. 4,4-Dimethylandrost-5-eno[2,3-d]isoxazol-17-one.

To a solution of 65 ml. of pyridine in 600 ml. of methylene dichloride held under a nitrogen atmosphere at room temperature was added portionwise 40 g. of chromium trioxide. The mixture was stirred for five minutes, and there was then added a solution of 17 g. of 4,4-dimethylandrost-5-eno[2,3-d]isoxazol-17β-ol (m.p. 196°-198° C., Manson et al., loc. cit.) in 160 ml. of methylene dichloride. The reaction mixture was stirred for ten minutes and then poured through a filter cel pad, then rinsed with methylene dichloride. The methylene dichloride solution was washed with 350 ml. of 2N hydrochloric acid and with 350 ml. of water, and dried over anhydrous magnesium sulfate mixed with activated carbon. The solution obtained by filtration was evaporated to remove the solvent, and the residue recrystallized from methanol to give 11.5 g. of 4,4-dimethylandrost-5-eno[2,3-d]isoxazol-17-one, m.p. 188°-190° C.

b. 4,4-Dimethyl-17α-pregn-5-en-20-yno[2,3-d]isoxazol-17β-ol was prepared from 34 g. of 4,4-dimethylandrost-5-eno[2,3-d]isoxazol-17-one and the Grignard reagent derived from acetylene and 100 ml. of 3M ethylmagnesium bromide in ether according to the procedure described above in Example 1. The resulting product was recrystallized from ether to give 16 g. of 4,4-dimethyl-17α-pregn-5-en-20-yno[2,3-d]isoxazol-17β-ol, m.p. 224°-227° C.; second crop 6 g., m.p. 223°-226° C. The product was identical in its properties with the same compound described by Manson et al, loc., cit., there named as 4,4-dimethyl-17α-ethinyl-17β-hydroxyandrost-5-eno[2,3-d]isoxazole.

EXAMPLE 3

21-Trifluoromethyl-17α-pregn-4-en-20-yno[2,3-d]isoxazol-17-ol [II; R is CF₃].

Ethylmagnesium bromide (0.25 mole, 85 ml. of 3 molar in ether) was added to 2 liters of dry ether under nitrogen. 3,3,3-Trifluoro-1-propyne (33.5 g., 0.35 mole) was passed into the solution over a period of 90 minutes. To the stirred solution was added 31.65 g. of 17-oxoandrost-4-eno[2,3-d]-isoxazole as a slurry in ether and benzene, and 10 g. of anhydrous magnesium chloride in tetramethylurea solution. The reaction mixture was stirred and heated at reflux for 24 hours. Saturated aqueous ammonium chloride solution was added with stirring, and the organic solution was washed with dilute hydrochloric acid and water. An emulsion formed which was filtered to give 6.61 g. of solid which was mainly unreacted starting material (17-oxoandrost-4-eno[2,3-d]isoxazole). The filtrate was concentrated to dryness, and the residue was dissolved in benzene and chromatographed on a column of 2 kg. of silica gel. Elution of the column with 5% ether in methylene dichloride gave 24 g. of 21-trifluoromethyl-17α-pregn-4-en-20-yno[2,3-d]isoxazol-17-ol containing slight amounts of starting material. Recrystallization of the latter first from acetonitrile and then from ethyl acetate gave 5.7 g. of 21-trifluoromethyl-17α-pregn-4-en-20-yno[2,3-d]-isoxazol-17-ol, m.p. 156°-158° C.

21-Trifluoromethyl-17α-pregn-4-en-20-yno[2,3-d]isoxazol-17-ol was found to possess estrogenic activity as measured by increase in uterine weight when administered subcutaneously to female rats at a dose level of 50.0 mg/kg/day × 3.

According to the foregoing procedures, 17-oxoandrost-4-eno[2,3-d]isoxazole can be caused to react with 1-propynylmagnesium bromide to afford 17α-(1-propynyl)androst-4-eno[2,3-d]-isoxazole [II; R is CH₃].

According to the foregoing procedures, 17-oxoandrostano[2,3-d]isoxazole (Manson et al., loc. cit.) can be caused to react with ethynylmagnesium bromide, 1-propynylmagnesium bromide or 3,3,3-trifluoro-1-propynylmagnesium bromide to afford, respectively, 17α-pregn-20-yno[2,3-d]isoxazol-17β-ol [I; R is H], 17α-(1-propynyl)androstano[2,3-d]isoxazol-17β-ol [I; R is CH₃], or 21-trifluoromethyl-17α-pregn-20-yno[2,3-d]isoxazol-17β-ol [I; R is CF₃].

EXAMPLE 4

Preparation of
5α,17α-pregnan-20-yno[2,3-d]isoxazol-17-ol [I; R is H].

Acetylene, purified by passage through traps of sulfuric acid and a column of basic alumina, was bubbled through 800 ml. of tetrahydrofuran held at −70° C. under anhydrous conditions. The acetylene addition was continued for one hour and then there was added 200 ml. of butyllithium (2.3M in hexane). The mixture was stirred for 30 minutes with continual addition of acetylene, followed by dropwise addition of a solution of 25.3 g. (0.08M) of 17-oxo-5α-androstano[2,3-d]isoxazole in 150 ml. of tetrahydrofuran. An extra 100 ml. of tetrahydrofuran was used for rinsing. The reaction mixture was stirred for three hours at −70° C. after which time thin layer chromatography indicated the absence of starting material. The resulting mixture was treated with 100 ml. of saturated ammonium chloride, added dropwise, and allowed to warm to 0° C. The aqueous and organic layers were separated, and the organic layer was concentrated in a rotary evaporator. The residue was partitioned between 500 ml. of chloroform and 500 ml. of water, and the chloroform solution was dried over anhydrous magnesium sulfate and the solvent removed by distillation. The residue was crystallized from 100 ml. of ethyl acetate to give 17.46 g. of 5α,17α-pregnan-20-yno[2,3-d]isoxazol-17-ol, m.p. 191°–193° C. A recrystallization from ethyl acetate gave 12.06 g., m.p. 196°–198° C.

EXAMPLE 5

Preparation of
17α-pregn-4-en-20-yno[2,3-d]isoxazol-17-ol [II; R is H].

Acetylene, purified by passage through sulfuric acid and an alumina column, was bubbled through 400 ml. of tetrahydrofuran held at −70° C. under anhydrous conditions for a period of one hour. There was then added in succession 100 ml. of butyllithium (2.5M in hexane), 250 ml. of tetrahydrofuran, a solution of 15.56 g. of 17-oxoandrost-4-eno[2,3-d]isoxazole in 500 ml. of warm tetrahydrofuran, and finally 250 ml. of warm tetrahydrofuran for rinsing. The reaction mixture was stirred at −70° to −40° C. for four hours and then treated with 50 ml. of saturated aqueous ammonium chloride. The tetrahydrofuran layer was decanted and dried over anhydrous magnesium sulfate. The solvent was removed by distillation and the residue crystallized from ethyl acetate to give 12.5 g. of 17α-pregn-4-en-20-yno[2,3-d]isoxazol-17-ol, m.p. 221°–224° C. containing traces of starting 17-oxo compound. Recrystallization of the latter twice from isopropyl alcohol and once from ethyl acetate gave 6.43 g. of pure 17α-pregn-4-en-20-yno[2,3-d]isoxazol-17-ol, m.p. 224°–226° C.

In order to obtain additional product and remove the 17-oxo starting material, 2.18 g. of carboxymethoxyamine hydrochloride and 1.36 g. of sodium acetate trihydrate in 10 ml. of water was added to the combined recrystallization mother liquors in 250 ml. of ethanol, and the mixture was heated at reflux for three hours. The solvent was removed by distillation in vacuo and the residue partitioned between 100 ml. of methylene dichloride and 100 ml. of 5% sodium bicarbonate solution. The methylene dichloride layer was washed with 100 ml. of 5% sodium bicarbonate solution and then with 100 ml. of 1N hydrochloric acid and dried over anhydrous magnesium sulfate. The solvent was removed and the residue crystallized from ethyl acetate to give 5.98 g. of 17α-pregn-4-en-20-yno[2,3-d]isoxazol-17-ol, m.p. 224°–226° C., total yield 12.41 g. (73.4%).

I claim:

1. A process for preparing a 17α-(2-R-ethynyl-17β-hydroxysteroido[2,3-d]isoxazole which comprises reacting a 17-oxosteroido[2,3-d]isoxadole devoid of substituents, other than the 17-oxo group, reactive with organometallic compounds, with (2-R-ethynyl)magnesium halide or (2-R-ethynyl)lithium wherein R is hydrogen, methyl or trifluoromethyl.

2. A process according to claim 1 for preparing a compound of the formula

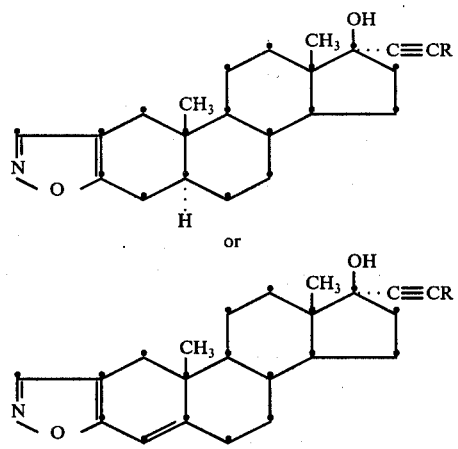

where R is H, CH₃ or CF₃, which comprises treating a compound of the formula

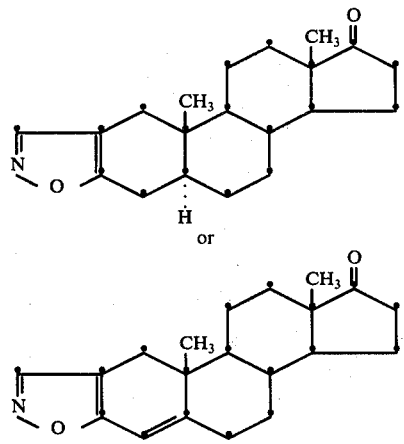

with a compound of the formula X-Mg-C≡CR where X is chlorine, bromine or iodine, or with a compound of the formula LiC≡CR, in an inert solvent under anhydrous conditions.

3. A process according to claim 2 wherein R is H.

4. A process for preparing 17α-pregn-4-en-20-yno[2,3-d]isoxazol-17-ol, according to claim 3, which comprises treating 17-oxoandrost-4-eno[2,3-d]isoxazole with ethynylmagnesium halide in an inert solvent under anhydrous conditions.

5. A process according to claim 4 wherein the ethynylmagnesium halide is ethynylmagnesium bromide.

6. A process for preparing 17α-pregn-4-en-20-yno[2,3-d]isoxazol-17-ol, according to claim 3, which comprises treating 17-oxoandrost-4-eno[2,3-d]isoxazole with monolithium acetylide in an inert solvent under anhydrous conditions.

7. A process for preparing 5α,17α-pregnan-20-yno[2,3-d]isoxazol-17-ol, according to claim 3, which comprises treating 17-oxo-5α-androstano[2,3-d]isoxazole with monolithium acetylide in an inert solvent under anhydrous conditions.

8. A process for preparing 4,4-dimethyl-17α-pregn-5-en-20-yno[2,3-d]isoxazol-17β-ol, according to claim 1, which comprises treating 4,4-dimethylandrost-5-eno[2,3-d]isoxazol-17-one with ethynylmagnesium halide in an inert solvent under anhydrous conditions.

9. A process according to claim 2 wherein R is $CF_3$.

10. A process for preparing 21-trifluoromethyl-17α-pregn-4-en-20-yno[2,3-d]isoxazol-17-ol, according to claim 9, which comprises treating 17-oxoandrost-4-eno[2,3-d]isoxazole with 3-trifluoro-1-propynylmagnesium halide in an inert solvent under anhydrous conditions.

11. 21-Trifluoromethyl-17α-pregn-4-en-20-yno[2,3-d]-isoxazol-17-ol.

* * * * *

UNITED STATES PATENT AND TRADEMARK OFFICE
CERTIFICATE OF CORRECTION

PATENT NO. : 4,055,562
DATED : October 25, 1977
INVENTOR(S) : Robert George Christiansen It is certified that error appears in the above–identified patent and that said Letters Patent are hereby corrected as shown below:

Column 1, line 49, "sith" should read --with--.

Column 6, line 6, Claim 1, "isoxadole" should read --isoxazole--.

Signed and Sealed this

Twenty-fourth Day of April 1979

[SEAL]

Attest:

RUTH C. MASON
Attesting Officer

DONALD W. BANNER
Commissioner of Patents and Trademarks